United States Patent [19]

Palermo

[11] Patent Number: 5,250,071
[45] Date of Patent: Oct. 5, 1993

[54] DETACHABLE EMBOLIC COIL ASSEMBLY USING INTERLOCKING CLASPS AND METHOD OF USE

[75] Inventor: Thomas J. Palermo, San Jose, Calif.

[73] Assignee: Target Therapeutics, Inc., Fremont, Calif.

[21] Appl. No.: 949,094

[22] Filed: Sep. 22, 1992

[51] Int. Cl.⁵ .................................. A61M 29/00
[52] U.S. Cl. .................................. 606/198; 128/898; 606/108
[58] Field of Search .............. 623/1, 12; 606/194, 606/152, 153, 108; 128/898

[56] References Cited

U.S. PATENT DOCUMENTS

| | | |
|---|---|---|
| 3,334,629 | 8/1967 | Cohn . |
| 4,739,768 | 4/1988 | Engelson . |
| 4,813,934 | 3/1989 | Engelson et al. ............ 604/99 |
| 4,884,579 | 12/1989 | Engelson . |
| 4,957,501 | 9/1990 | Lahille et al. ............ 606/200 |
| 4,994,069 | 2/1991 | Richart et al. . |
| 5,108,407 | 4/1992 | Geremia et al. ............ 606/108 |
| 5,109,867 | 5/1992 | Twyford ............ 604/283 |
| 5,122,136 | 6/1992 | Guglielmi et al. ............ 606/32 |

*Primary Examiner*—Jerome L. Kruter
*Attorney, Agent, or Firm*—Morrison & Foerster

[57] ABSTRACT

This invention is a surgical instrument and specifically is a device for delivering an embolic coil to a selected site within the vasculature of a human body via use of a catheter. In particular, the device uses embolic coils having interlocking clasps on the coils which are secured to each other by a control wire within the catheter. Retraction of the control wire into the catheter body uncouples the distal coil.

21 Claims, 5 Drawing Sheets

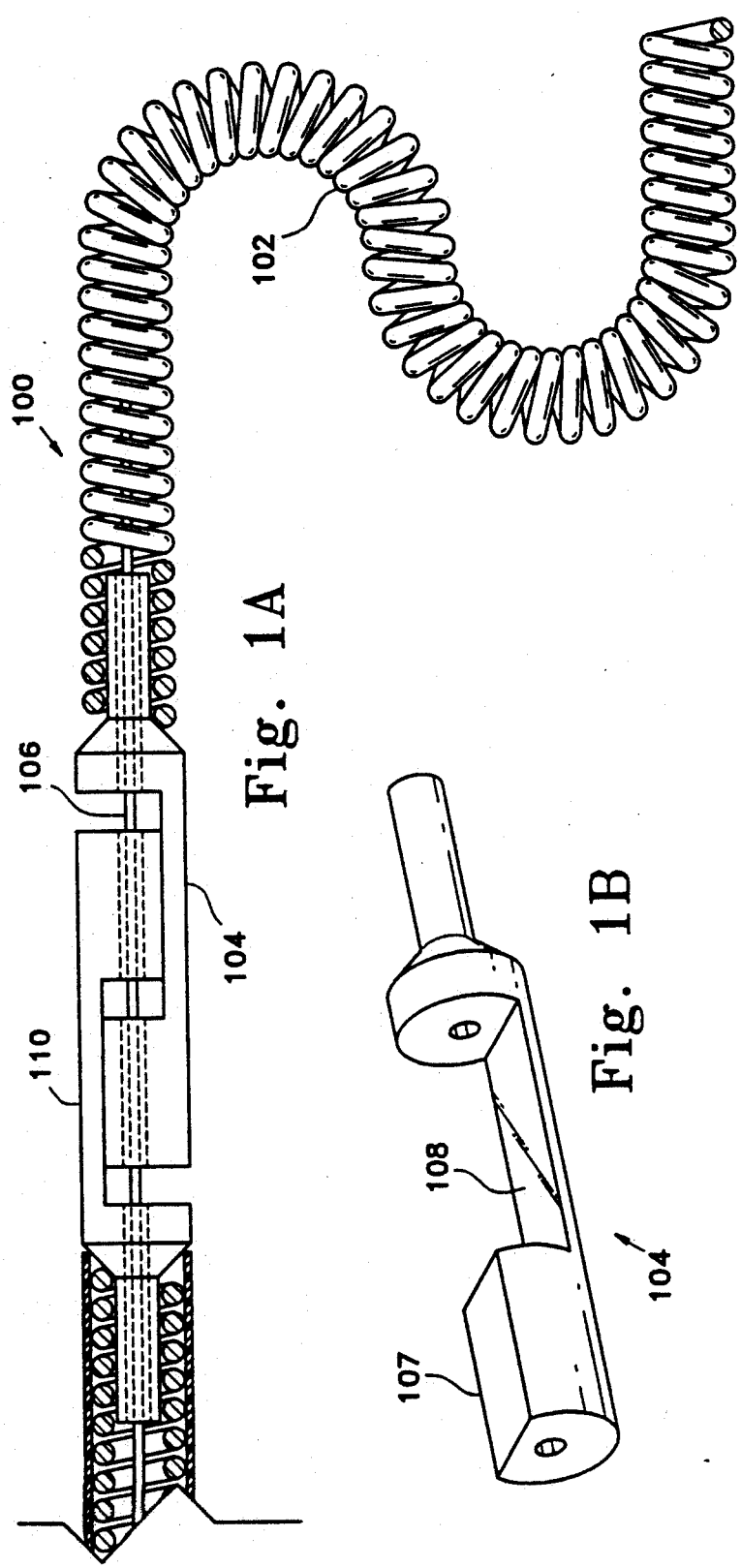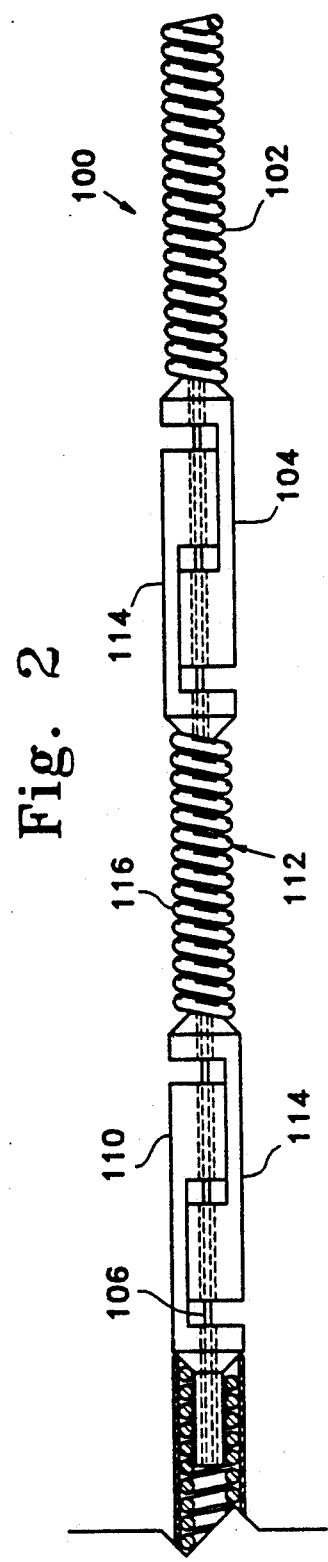

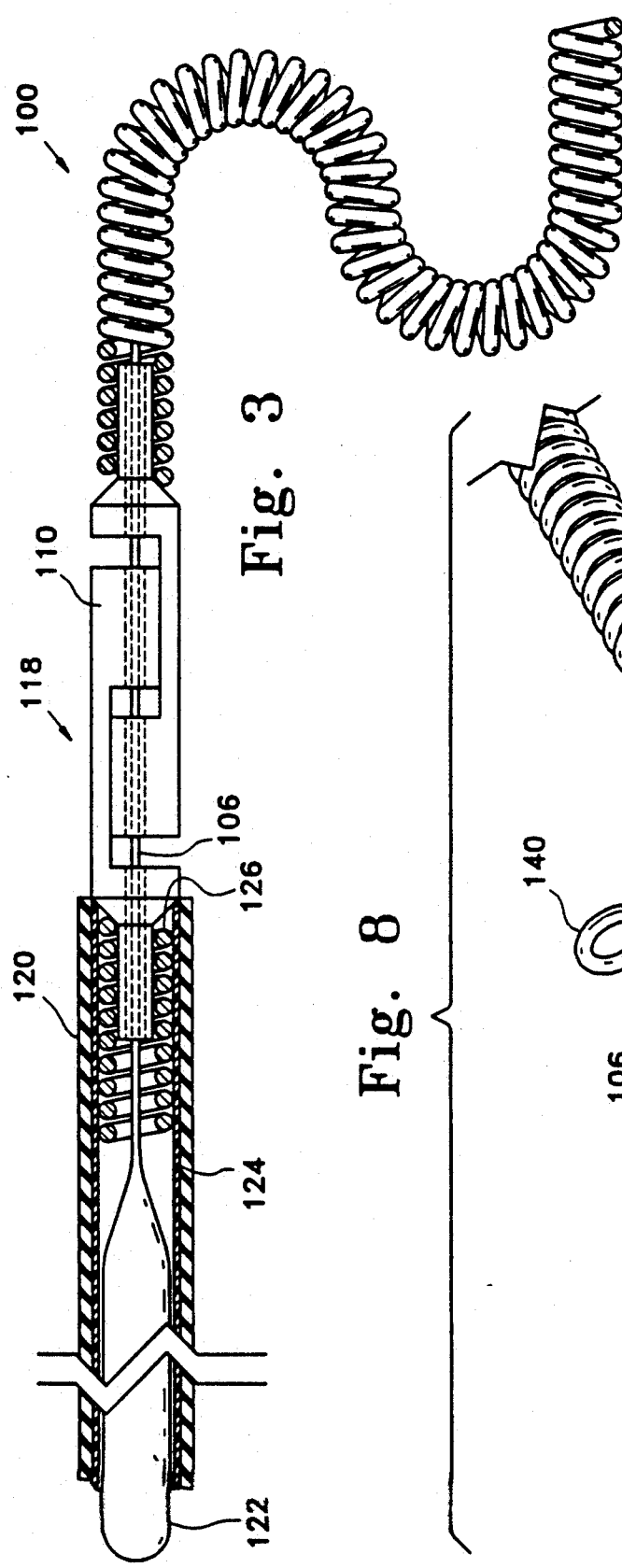
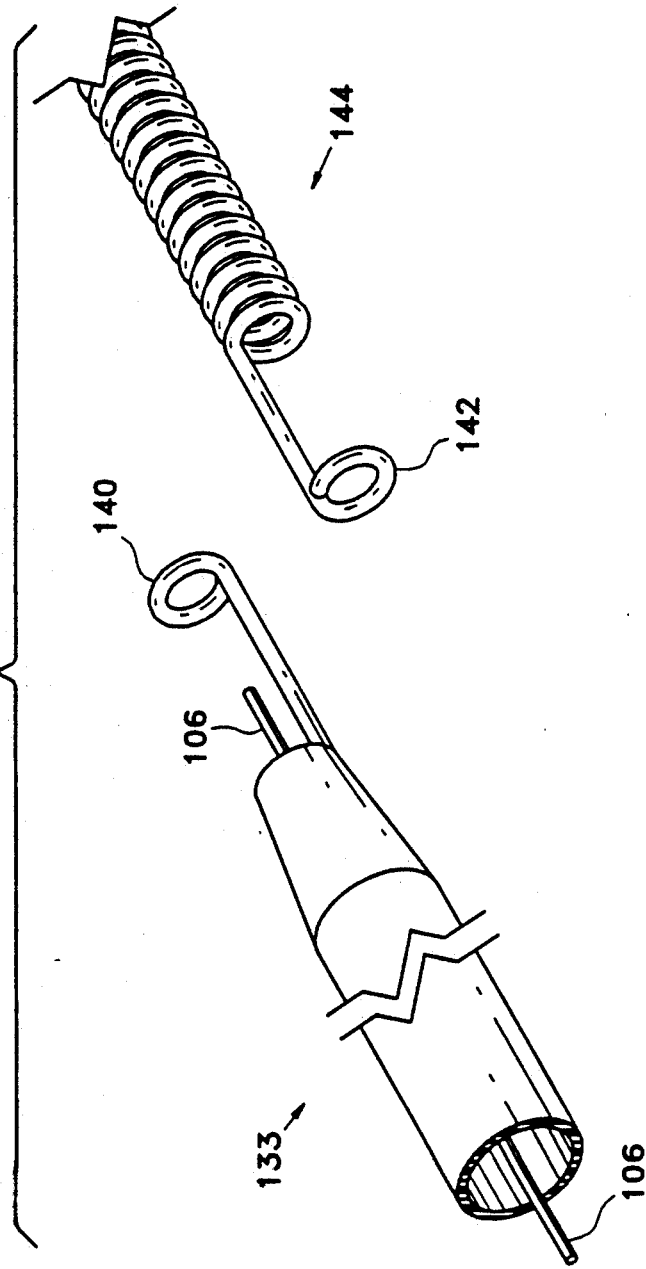
Fig. 3
Fig. 8

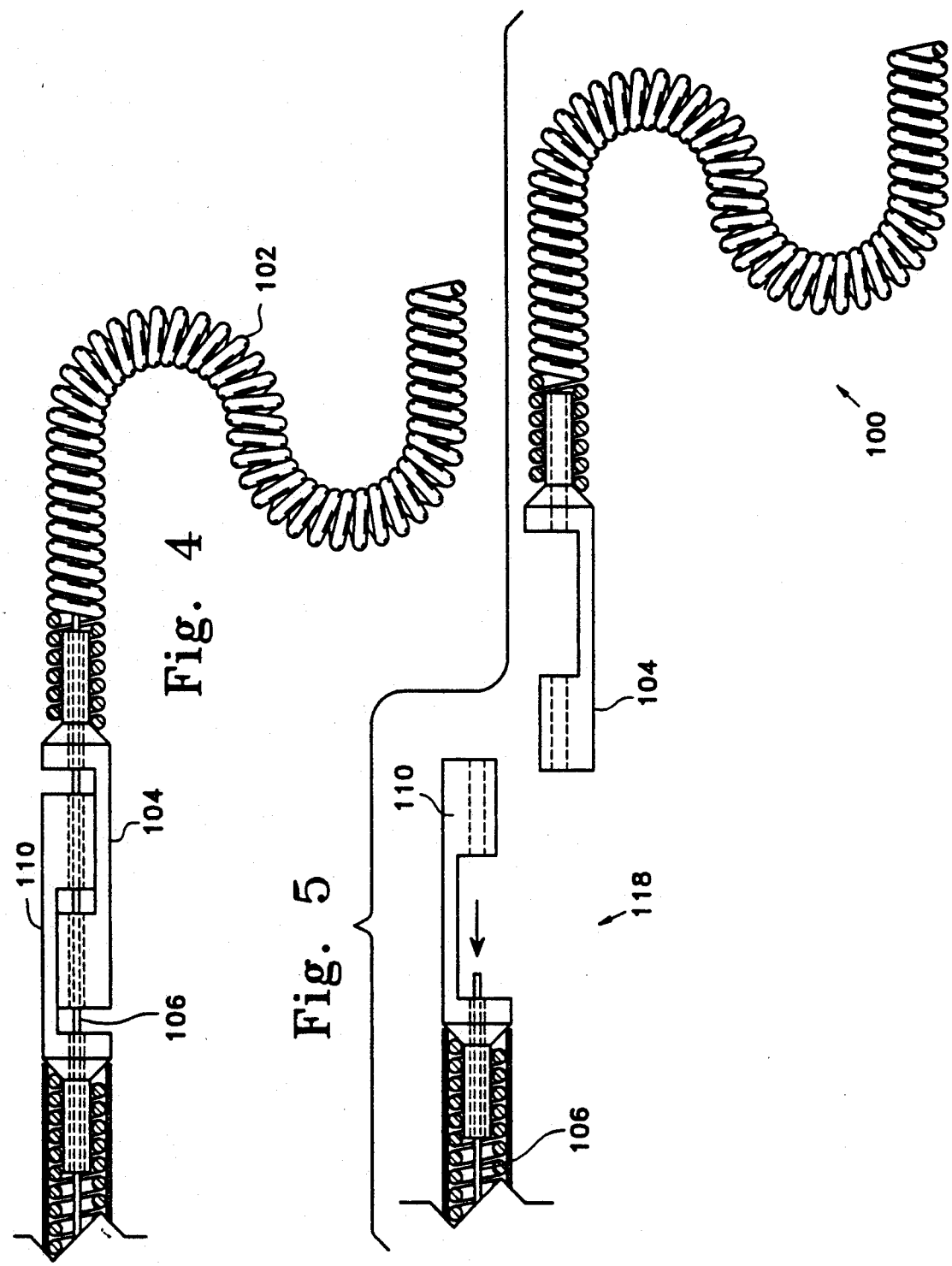

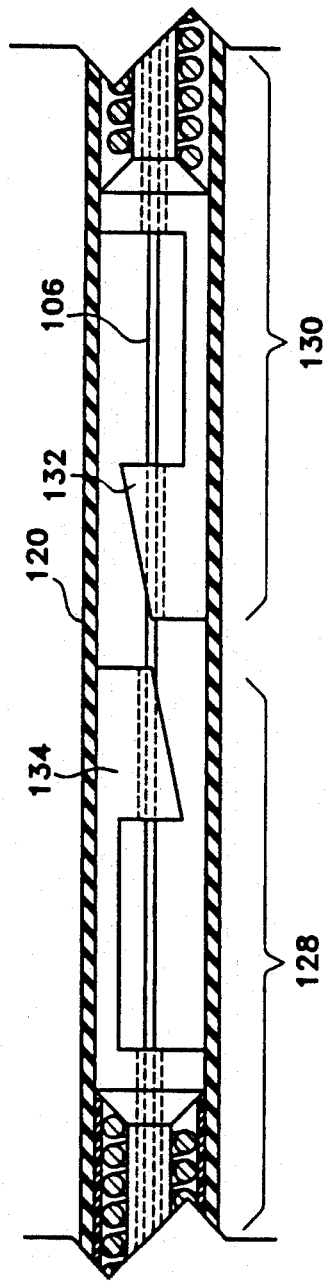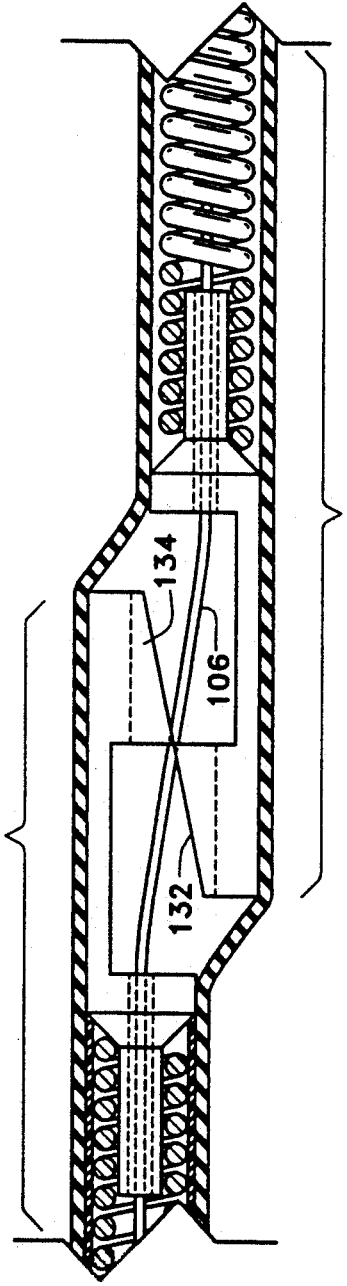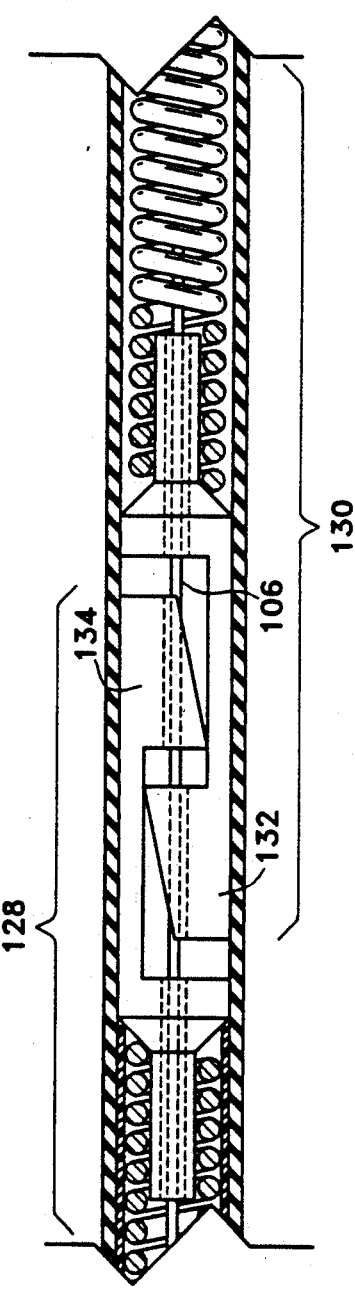

DETACHABLE EMBOLIC COIL ASSEMBLY USING INTERLOCKING CLASPS AND METHOD OF USE

FIELD OF THE INVENTION

This invention is a surgical instrument and specifically is a device for delivering embolic coils to a selected site within the vasculature of a human body via use of a catheter. In particular, the device uses embolic coils having interlocking clasps on the coils which are secured to each other by a control wire within the catheter. Retraction of the control wire into the catheter body uncouples the distal coil.

BACKGROUND OF THE INVENTION

The endovascular treatment of a variety of vascular maladies throughout the body is an increasingly more important form of therapy. Catheters have been used to place various treatment materials, devices, and drugs within arteries and veins in the human body. Examples of these devices and their use in such treatments are shown in commonly assigned U.S. patent application Ser. Nos. 07/806,898 ("Detachable Pusher-Vasoocclusive Coil Assembly with Threaded Coupling") and 07/806,912 ("Detachable Pusher-Vasoocclusive Coil Assembly with Interlocking Ball and Keyway Coupling"). These show methods and devices for delivery of coils or wires within the human body to sites such as aneurysms, to occlude those sites. Coils such as are discussed in those two documents (as well as in U.S. Pat. No. 4,994,069), may be of a regular or helical configuration or assume a random convoluted configuration at the site. The coils normally are made of a radiopaque, biocompatible metal such as platinum, gold, tungsten, or alloys of these and other metals.

In treating aneurysms it is common to place a number of coils within the aneurysm. The coils occlude the site by posing a physical barrier to blood flow and by promoting thrombus formation at the site.

Coils have typically been placed at the desired site within the vasculature using a catheter and a pusher. The site is first accessed by the catheter. In treating peripheral or neural conditions requiring occlusion, the sites are accessed with flexible, small diameter catheters such as those shown in U.S. Pat. Nos. 4,739,768 and 4,813,934. The catheter may be guided to the site through the use of guidewires (see U.S. Pat. No. 4,884,579) or by flow-directed means such as balloons placed at the distal end of the catheter. Use of guidewires involves the placement of relatively long, torqueable proximal wire sections within the catheter attached to more flexible distal end wire sections designed to be advanced across sharp bends at vessel junctions. The guidewire is visible using x-ray and allows a catheter to be placed in extremely tortuous vessels, even though surrounded by soft tissue such as the brain.

Once the site has been reached, the catheter lumen is cleared by removing the guidewire (if a guidewire has been used), and the coil is placed into the proximal open end of the catheter and advanced through the catheter with a pusher. Pushers are wires having a distal end that is adapted to engage and push the coil through the catheter lumen as the pusher is advanced through the catheter. When the coil reaches the distal end of the catheter, it is discharged from the catheter by the pusher into the vascular site. This technique of discharging the coil from the distal end of the catheter has a number of undesirable limitations. First, because of the plunging action of the pusher and the coil, the positioning of the coil at the site cannot be controlled to a fine degree of accuracy. Second, once the coil has left the catheter, it is difficult to reposition or retrieve the coil if such is desired.

Several techniques have been developed to enable more accurate placement of coils within a vessel. In one technique (U.S. Pat. No. 5,122,136, issued Jun. 16, 1992) the coil is bonded via a metal-to-metal joint to the distal end of the pusher. The pusher and coil are made of dissimilar metals. The coil-carrying pusher is advanced through the catheter to the site and a low electrical current is passed through the pusher-coil assembly. The current causes the joint between the pusher and the coil to be severed via electrolysis. The pusher may then be retracted leaving the detached coil at an exact position within the vessel. In addition to enabling more accurate coil placement, the electric current may facilitate thrombus formation at the coil site. The only perceived disadvantage of this method is that the electrolytic release of the coil requires a period of time so that rapid detachment of the coil from the pusher does not occur.

Another technique for detaching an embolic coil is shown in commonly assigned U.S. patent application Ser. No. 07/806,912. In that document, a coil having an enlarged portion is mated with a pusher having a keyway adapted to receive the enlarged portion of the coil in an interlocking relationship is covered by a coaxial member about the pusher and the coil. The coaxial member is movable by sliding the member axially. As the coaxial member is moved away from the junction where the coil's member engages the member of the keyway of the pusher, the coil disengages and the pusher is removed.

Another device for placement of coils is shown in commonly assigned U.S. patent application Ser. No. 07/806,898. This device includes a coil having a helical portion at one end and a pusher which is threaded to the inside of the helical coil by the use of a threaded section on the outside of the pusher. The device operates to release the coil by engaging the proximal end of the coil with a sleeve while the pusher is unthreaded. Once the pusher is free, the sleeve may be used to push the coil out into the treatment area.

Another method of placing an embolic coil is shown in U.S. Pat. No. 5,108,407. This patent shows the use of a device in which embolic coils are separated from the distal end of a catheter by the use of heat-releasable adhesive bonds. The coil adheres to the therapeutic device via a mounting connection using a heat sensitive adhesive. Laser energy is transferred through a fiber optic cable, which cable terminates at the connector. The connector becomes warm and releases the adhesive bond between the connector and the coil.

None of these disclosed devices suggest the use of an interlocking latch which allows an embolic coil to be precisely positioned and then released upon retraction of a control wire positioned within that latch.

SUMMARY OF THE INVENTION

This invention is a device for placing detachable coils within the vasculature of the human body so to occlude that site with the coils. The device includes a coil that carries an interlocking clasp at at least one end of the coil, preferably at its proximal end and a pusher (positioned within the catheter) which has a clasp at its distal end which interlocks with the clasp situated on the coil. The coils may have interlocking clasps at each end thereby allowing a number of coils to be strung together and yet individually released. A control wire passing through the catheter, the pusher assembly, the pusher clasp, and the coil clasp releases the coil as the control wire is retracted through axial passageways or openings provided in the two clasps.

Another portion of the invention is a method for occluding a selected vascular site comprising the steps of: (a) accessing the site with a distal end of a catheter; (b) advancing the assembly described above through the catheter with the coil clasp and the pusher clasp interlocked to a position out the end of the distal end of the catheter; (c) withdrawing the control wire from the two clasps to thereby detach the coil from the pusher; and (d) withdrawing the catheter and pusher from the vessel.

BRIEF DESCRIPTION OF THE DRAWINGS

FIGS. 1A and 1B show, respectively, a partial sectional view of a pusher assembly and an engaged coil assembly having an interlocking clasp at only one end and a front three-quarters view of one variation of the interlocking clamp.

FIG. 2 shows a series of coil assemblies having either one or two interlocking clasps at their ends.

FIG. 3 shows deployment of the interlocking coil within a catheter.

FIGS. 4 and 5 show the operation of the assembly as it places a coil within a target site.

FIGS. 7A, 7B, and 7C show a method of attaching coils having the interlocking clasp shown in FIGS. 6A and 6B to a pusher body within the catheter lumen.

FIG. 8 shows a variation of the invention in which both the coils and the pusher body have simple loops as interlocking clasps.

DESCRIPTION OF THE INVENTION

Figures 6A, 6B:
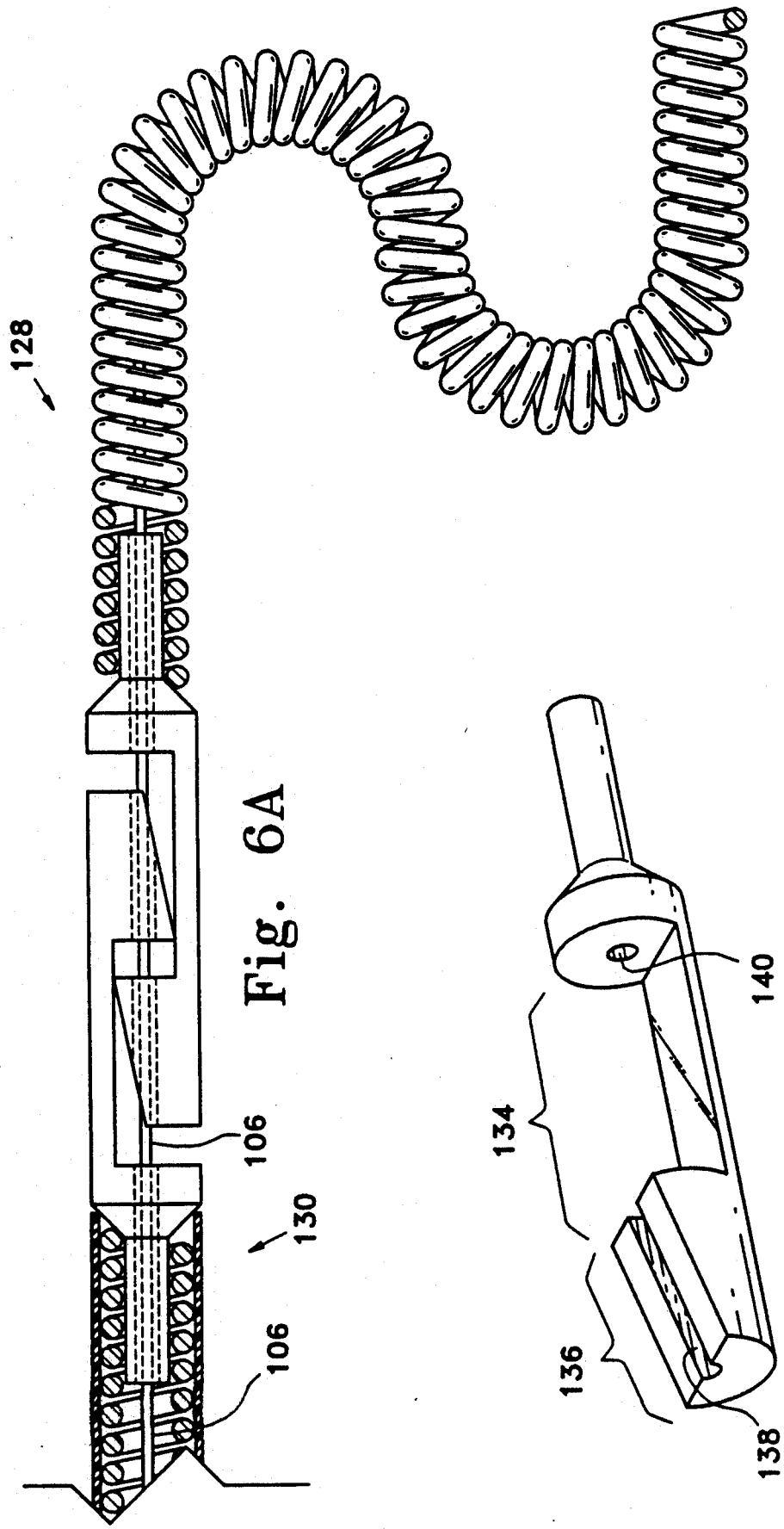
FIGS. 6A and 6B show, respectively, a partial sectional view of a pusher assembly and an engaged coil assembly having a variation of an interlocking clasp and a front three-quarter view of that variation of the interlocking clasp.

The coil assembly (100) is shown in FIG. 1. The coil (102) is shown as helical in form, although it may be any other suitable form. The coil should be of a size sufficiently small that it may be advanced through a catheter that is appropriately sized for accessing the targeted vascular site. For instance, when accessing a brain aneurysm in a small vessel, an appropriately sized catheter is quite small and very flexible. The coil in such a situation must be small enough to fit through the catheter and out its distal end at the treatment site.

The coil is desirably made up of a radiopaque, physiologically compatible material. The material may be platinum, gold, tungsten, or alloys of these. Certain polymers are also suitable as coil material either alone or in conjunction with metallic markers providing radiopacity. These materials are chosen so that the procedure of locating coils within the vessel may be viewed using radiography. However, it is also contemplated that these coils may be made of various other biologically inert polymers or of carbon fiber.

The size of the coil and its constituent winding will depend upon the use to which the coil will be placed. For occluding peripheral or neural sites, the coils will typically be made of 0.05 to 0.15 mm diameter wire (platinum or platinum/tungsten alloy) that is wound to have an inner diameter of 0.15 to 1.5 mm with a minimum pitch— that is to say that the pitch is equal to the diameter of the wire used in the coil. The length of the coil will normally be in the range of 0.5 to 60 cm, preferably 0.5 to 40 cm.

If desired, the coil may be formed in such a way that the coil is essentially linear as it passes through the catheter and yet assumes a randomly oriented relaxed condition after it is released from the distal end of the catheter. A discussion of this variation may be found in U.S. Pat. No. 4,994,069.

Fixedly attached to coil (102), as is shown in FIG. 1A, is interlocking clasp (104). Interlocking clasp (104) as is depicted in the front three-quarter view in FIG. 1B, has an interior passageway allowing the control wire (106) to pass completely therethrough. As is shown in FIG. 1A, the male portion of the next adjacent interlocking clasp (110) fits into the area (108) left within clasp (104) so to allow the interlocking to take place. Said another way, the distal portion of interlocking clasp (104) is generally cylindrical in shape but has a surface (107), which may be cut or milled away, allowing the portion to mesh within the middle area (108) of an adjacent clasp. The proximal section is adapted for attaching to a coil or to a pusher assembly. The attachment may be by welding, soldering, gluing, or the like. With a control wire (106) passing through the axis of both interlocking clasps (104) and (110), the two are locked together. As is shown in FIG. 1A, the control wire may extend through the length of coil (102).

FIG. 2 shows an intermediate coil assembly (110) comprising coil (102) and interlocking clasp (104) (joined with coil assembly (112) which has interlocking clasp (114) fixedly attached at both ends of the intervening coil (116). As was the situation in FIG. 1A, the proximal interlocking clasp (114) is joined by control wire (106) with interlocking clasp (110). In this way, a significant number of coils (112) may be loaded onto a control wire (106) and delivered to the treatment site without removal of the control wire from the catheter.

FIG. 3 shows the relationship of coil assembly (100) and the pusher assembly (118) with its distal interlocking clasp (110) as it fits within catheter sheath (120). Also shown is movable inner core member (122) and the sheath (124) which fits within catheter sheath (120) and supports interlocking clasp (110). Shown in FIG. 3 is the stiffener spring (126) which provides form and support for the distal end of the pusher assembly (118) and in particular rigidly adheres to interlocking clasp (110). Inner core member (122) allows the control wire (106) to be moved axially along the interior of the catheter sheath (120) and the pusher assembly (118). Movement of the inner core member (122) in a proximal direction permits uncoupling of the coil as will be discussed in more detail below.

The length of pusher assembly (118) will be such as to be capable of being advanced entirely through the catheter to place coil (102) at the target site but yet with a sufficient portion of the proximal end of the pusher assembly (118) protruding from the proximal end of the catheter to enable the control wire (106) to be manipulated. For use in peripheral or neural surgeries, the pusher will normally about 100–200 cm in length, more normally 130–180 cm in length. The diameter of the pusher assembly (118) is usually in the range of 0.25 to about 0.90 mm.

As indicated previously, conventional catheter insertion and navigational techniques involving guidewires or flow-directed devices may be used to access the site with a catheter. Once the distal end of the catheter is positioned at the site, often by locating its distal end through the use of radiopaque marker material and radiography, the catheter is cleared. For instance, if a guidewire has been used to position the catheter, it is withdrawn from the catheter and then the pusher assembly (118) having coil assembly (100) at the distal end is advanced through the catheter. The pusher assembly (118) is advanced past the distal end of the catheter so that the coil is free of the catheter and with the coil positioned precisely at the desired treatment site.

As is shown in FIGS. 4 and 5, control wire (106) is withdrawn from the junction between coil interlocking clasp (104) and the other interlocking clasp (110). Coil assembly (100) is then free. The entire catheter may then be removed or the pusher assembly (118) may be withdrawn from the catheter lumen to provide for installation of other coils. If additional coils are to be placed at the target site, the procedure is repeated. After the desired number of coils have been placed at the site, the catheter is withdrawn from the vessel.

FIG. 6A shows a variation in which coil assembly (128) is interlocked with pusher assembly (130) by control wire (106). The depicted coil assembly (128) and pusher assembly (130) are different in that they incorporate the interlocking clasp (132) design shown more clearly in FIG. 6B. The interlocking clasp (132), as with the clasp depicted in FIG. 1B, utilizes an open area (134) within the clasp (132) to accept the mating ramp latch (136) from another similar clasp. The ramp latch (136) typically has a slot (138) and a passageway (140) to permit passage of the control wire through the clasp (132) from end to end without obstruction.

The ramp latch (136) allows easy assembly of a string of coils within the catheter for subsequent placement using the device.

Such an assembly process is shown in FIGS. 7A, 7B, and 7C.

FIG. 7A shows a pusher assembly (130) approaching a coil assembly (128) which has been previously placed within a catheter sheath (120). The distal interlocking clasp (132) on the pusher assembly (130) is positioned to interlock with the proximal interlocking clasp (134) on the coil assembly (128).

FIG. 7B shows the two interlocking clasps (132 and 134) as they approach their respective ramps contacting and causing the two clasps to displace axially within the catheter sheath.

FIG. 7C shows the location of the coil assembly (128) and the pusher assembly (132) after the respective clasps are interlocked and the control wire (106) has been placed through the passageways within the clasps.

FIG. 8 shows an elegantly simple variation of the invention in which the pusher (138) is a tubing member having a control wire (106) within its core. The clasp portion (140) is a simple loop comprising, e.g., wire or small rod. The corresponding interlocking loop (142) on the coil (144) forms the junction with the clasp on the pusher.

The variation of the invention shown in FIGS. 6A, 6B, 7A, 7B, 7C, and 8 may be placed within the vasculature in the same manner as shown for the variation shown in FIGS. 4 and 5.

Modifications of the device described above and methods of using it in keeping with this invention that are apparent to those having skill in this mechanical and surgical instrument design art and related fields are intended to be within the scope of the claims which follow.

I claim:

1. A detachable coil assembly for use in occluding a selected vascular site within a vessel comprising a coil having, on at least one end, an interlocking shaped clasp means having an axis and an axial passageway generally colinear with the coil, the axial passageway and the interlocking clasp means to interlock with similar shaped clasp means by passing a control wire through the axial passageway and to uncouple from said similar shaped clasp means by axially withdrawing the control wire from the shaped clasp means.

2. The assembly of claim 1 where the coil is a helical coil.

3. The assembly of claim 2 where the coil has a random configuration.

4. The assembly of claim 2 where the coil has a straight configuration.

5. The assembly of claim 1 where the coil assembly has interlocking shaped clasp means at each end.

6. The assembly of claim 1 in which the interlocking shaped clasp means having an axial passageway comprises a distal portion of a generally cylindrical shape, a middle portion adapted to accept said cylindrical distal portion from a similar interlocking shaped clasp means, and a proximal section adapted for attaching to the coil.

7. The assembly of claim 6 in which the interlocking shaped clasp means having an axial passageway therethrough comprises a generally cylindrical distal portion having a ramp adapted to engage a ramp on a similar interlocking shaped clasp means, a middle portion adapted to accept a cylindrical portion with a ramp or a similar interlocking shaped clasp means, and a proximal portion adapted for attaching to the coil and having a passageway therethrough.

8. The assembly of claim 1 additionally comprising a control wire therethrough.

9. The assembly of claim 8 additionally comprising one or more coil assemblies interlocked by the control wire.

10. A combination pusher assembly-coil assembly for use in occluding a selected vascular site within a vessel comprising:
 (a) a coil having, on at least one end, an interlocking shaped clasp means having an axis and an axial passageway generally colinear with the coil, the axial passageway and the interlocking shaped clasp means to interlock with a similar shaped clasp means by passing a control wire through the axial passageway and to uncouple from said similar shaped clasp means by axially withdrawing the control wire from the similar clasp means;
 (b) a pusher assembly comprising a tubular pusher sheath having a proximal end and a distal end and adapted to fit within a catheter sheath and having a continuous passageway therethrough for passage of a control wire from the distal end of the pusher sheath to the proximal end of the pusher sheath, and an interlocking shaped clasp means located at the distal end of the pusher sheath and said shaped clasp means connected to the distal end of the pusher assembly; and
 (c) a control wire suitable for passage through the pusher passageway and the coil axial passageway.

11. The assembly of claim 10 where the coil is a helical coil.

12. The assembly of claim 11 where the coil has a random configuration.

13. The assembly of claim 11 where the coil has a straight configuration.

14. The assembly of claim 10 additionally comprising a catheter sheath disposed about the pusher sheath.

15. The assembly of claim 10 additionally comprising more than one coil.

16. The assembly of claim 10 in which the interlocking shaped clasp means comprise a distal portion of a generally cylindrical shape, but having a middle portion adapted to accept said cylindrical distal portion from a similar shaped clasp means to allow interlocking with said similar shaped clasp means, and a proximal section adapted for attaching to the coil having a passageway therethrough.

17. The assembly of claim 10 in which the interlocking shaped clasp means comprise a generally cylindrical distal portion having a ramp adapted to engage a ramp of a similar interlocking shaped clasp means, a middle portion adapted to accept a cylindrical portion with a ramp on a similar interlocking shaped clasp means, and a proximal portion adapted for attaching to the coil and having a passageway therethrough.

18. A process for the placement of embolic coils at a selected vascular site comprising the steps of:

a) introducing to a selected site an embolic coil having, on at least one end of said coil, an interlocking shaped clasp means and having an axis generally colinear with the coil and an axial passageway through the coil, the axial passageway and the interlocking clasp means to interlock with similar shaped clasp means by passing a control wire through the axial passageway and to uncouple from said similar shaped clasp means by withdrawing a control wire from the shaped clasp means, and b) withdrawing the control wire from the shaped clasp means.

19. The process of claim 18 in which the coil is helical.

20. The process of claim 19 where the coil has a random configuration.

21. The process of claim 19 where the coil has a straight configuration.

* * * * *